United States Patent [19]

Nakagawa et al.

[11] 4,072,683
[45] Feb. 7, 1978

[54] 3,4-DIHYDROCARBOSTYRIL DERIVATIVES

[75] Inventors: Kazuyuki Nakagawa, Tokushima; Minoru Uchida, Komatsushima; Hiroaki Oka, Tokushima, all of Japan

[73] Assignee: Otsuka Pharmaceutical Co., Ltd., Tokyo, Japan

[21] Appl. No.: 630,631

[22] Filed: Nov. 10, 1975

[30] Foreign Application Priority Data

Nov. 8, 1974 Japan .................................. 49-129386
Nov. 8, 1974 Japan .................................. 49-129387

[51] Int. Cl.$^2$ .................. C07D 215/22; C07D 215/26; A61K 31/47
[52] U.S. Cl. ............................ 260/288 R; 260/286 R; 260/289 K; 424/258
[58] Field of Search ...................... 260/288 R

[56] References Cited

U.S. PATENT DOCUMENTS

| | | | |
|---|---|---|---|
| 3,340,266 | 9/1967 | Howe et al. ................. | 260/288 R |
| 3,910,924 | 10/1975 | Tamura et al. .............. | 260/288 R |
| 3,919,239 | 11/1975 | Nakagawa et al. ........... | 260/288 R |
| 3,953,456 | 4/1976 | Nakagawa et al. ........... | 260/288 R |

FOREIGN PATENT DOCUMENTS

| | | | |
|---|---|---|---|
| 42-1182 | 1/1967 | Japan ........................ | 260/288 R |
| 640,510 | 7/1964 | Netherlands ................ | 260/288 R |
| 1,058,822 | 2/1967 | United Kingdom ............ | 260/288 R |

*Primary Examiner*—Alton D. Rollins
*Assistant Examiner*—Mary Vaughn

[57] ABSTRACT

Novel (3'-alkylamino-2'-hydroxy)propoxy-3,4-dihydrocarbostyril derivatives having β-adrenergic nerves blocking activity and hypotensive activity and useful as a remedy for angina pectoris, irregular pulse and hypertension, etc., represented by the formula,

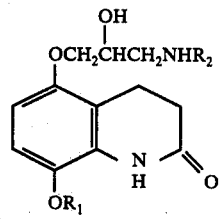

wherein $R_1$ is hydrogen, $C_1$–$C_4$ alkyl or aralkyl and $R_2$ is $C_1$–$C_4$ alkyl, are prepared by reacting a 3,4-dihydrocarbostyril derivative represented by the formula,

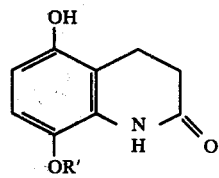

wherein $R_1$ is $C_1$–$C_4$ alkyl or aralkyl, with an epihalogenohydrin represented by the formula,

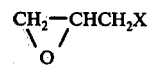

wherein X is halogen, reacting the resulting product with an alkylamine represented by the formula,

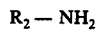

wherein $R_2$ is as defined above, and, if necessary, reducing the resulting product.

8 Claims, No Drawings

3,4-DIHYDROCARBOSTYRIL DERIVATIVES

The present invention relates to novel 3,4-dihydrocarbostyril derivatives. More particularly, the invention pertains to novel 5-(3'-alkylamino-2'-hydroxy)-propoxy-8-substituted-3,4-dihydrocarbostyril derivatives having β-adrenergic nerves blocking activity and hypotensive activity and useful as a remedy for angina pectoris, irregular pulse and hypertension, etc.

It is known that certain carbostyril derivatives exhibit useful pharmacological activities. Representative compounds of this type are those disclosed in Japanese Patent Publication Nos. 1182/1967 and 38789/1971 and Chemical Abstracts, Vol. 62, 1b, 212e (1965), etc. However, the above-mentioned references do not teach that compounds having a 3-substituted aminopropoxy group at 5-, 6-, 7- or 8-position of the carbostyril moiety exhibit an excellent blocking activity on β-adrenergic nerves. Further, Belgian Pat. No. 794,669 disclose 3,4-dihydroxycarbostyril derivatives of the formula,

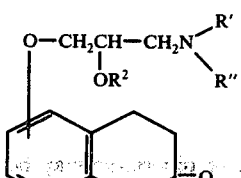

wherein $R^1$ is hydrogen, $C_1$–$C_4$ alkyl, aralkyl or $C_2$–$C_4$ alkenyl, $R^2$ is hydrogen or acyl of the formula $COR^3$ wherein $R^3$ is $C_1$–$C_4$ alkyl, phenyl or 3,4,5-trimethoxyphenyl, and R' and R" may be the same or different and each are hydrogen, $C_1$–$C_4$ alkyl, aralkyl or cycloalkyl or R' and R", when taken together with the nitrogen atom to which they are attached may form a heterocyclic group which may contain an additional nitrogen atom or an oxygen atom as a ring member, and pharmaceutically acceptable acid addition salts thereof, with the proviso that when substitution is at the 5-position and $R^1$ and $R^2$ are hydrogen, R' and R" are not simultaneously hydrogen and $C_1$–$C_4$ alkyl. The 3,4-dihydrocarbostyril derivatives of the present invention are one of the metabolic products of compounds of the above-mentioned Belgian patent specification represented by the formula,

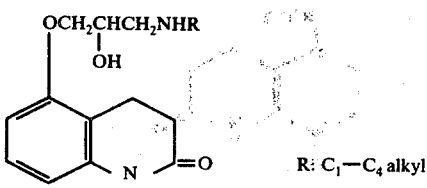

R: $C_1$–$C_4$ alkyl and their β-adrenergic nerves blocking activity is lower than that of the compounds of the Belgian patent specification but their hypotensive activity is higher.

According to the present invention, there are provided novel 3,4-dihydrocarbostyril derivatives represented by the formula,

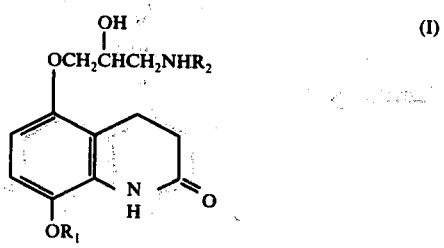

(I)

wherein $R_1$ is hydrogen, $C_1$–$C_4$ alkyl or aralkyl and $R_2$ is $C_1$–$C_4$ alkyl.

The $C_1$–$C_4$ alkyl groups in the formula (I) include methyl, ethyl, propyl, isopropyl, sec-butyl, tert-butyl, etc. The aralkyl groups include benzyl, phenethyl, etc.

The 3,4-dihydrocarbostyril derivatives of formula (I) can be prepared by reacting a 3,4-dihydrocarbostyril derivative represented by the formula,

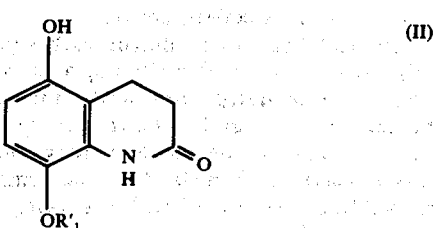

(II)

wherein $R'_1$ is $C_1$–$C_4$ alkyl or aralkyl, with an epihalogenohydrin represented by the formula,

(IV)

wherein X is halogen, reacting the resulting product with an alkylamine represented by the formula, $$R_2—NH_2 \tag{V}$$

wherein $R_2$ is as defined above, and, if necessary, reducing the resulting product.

The 3,4-dihydrocarbostyril derivatives of formula (II) which may be used as the starting material in the present invention are novel compounds and are obtained, for example, by the following route of

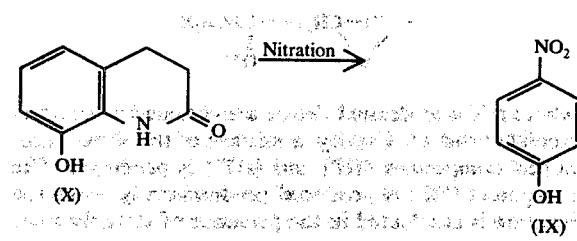

Reduction→ 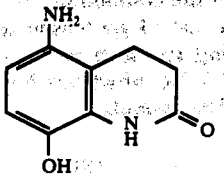

(VIII)

Oxidation→ 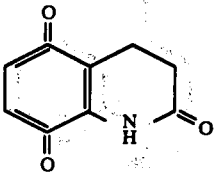 Reduction→

(VII)

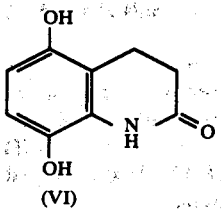 Alkylation or aralkylation→ 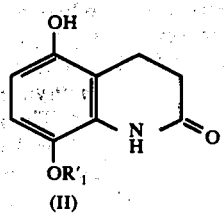

(VI)  (II)

-continued wherein R'₁ is as defined above.

Known 8-hydroxy-3,4-dihydrocarbostyril of formula (X) is first reacted with a nitrating agent such as a mixture of concentrated nitric acid, nitric anhydride or fuming nitric acid and acetic acid, acetic anhydride or sulfuric acid to obtain 8-hydroxy-5-nitro-3,4-dihydrocarbostyril of formula (IX). The compound of formula (IX) is then reacted with a reducing agent such as a mixture of stannous chloride, tin, iron or zinc and hydrochloric acid or sulfuric acid, or hydrogenated in the presence of a catalyst such as palladium-carbon to obtain 8-hydroxy-5-amino-3,4-dihydrocarbostyril of formula (VIII). The compound of formula (VIII) is then reacted with an oxidizing agent such as ferric chloride, chromic acid, a chromate, $K_2CrO_7 + H_2SO_4$, $KMnO_4 + H_2O$ or $MnO_2 + H_2SO_4$ to obtain 5,8-dioxo-3,4,5,8-tetrahydrocarbostyril of formula (VII). The compound of formula (VII) is then reacted with a reducing agent such as sulfur dioxide or sodium bisulfite or zinc and acetic acid to obtain 5,8-dihydroxy-3,4-dihydrocarbostyril of formula (VI). Finally, the compound of formula (VI) is reacted with an alkylating agent such as methyl iodide or dimethyl sulfate or with an aralkylating agent such as benzyl chloride to alkylate or aralkylate the hydroxy group at 8-position. The alkylation or aralkylation usually occurs at 8-position only, but occurs at both 5- and 8-positions as the case may be. Thus, the 3,4-dihydrocarbostyril derivatives of formula (II) used as the starting material in the present invention are obtained.

The present invention is practiced by reacting the 3,4-dihydrocarbostyril derivatives of formula (II) with an epihalogenohydrin of formula (IV) and then reacting the resulting product with an alkylamine of formula (V).

The reaction of the 3,4-dihydrocarbostyril derivatives of formula (II) with the epihalogenohydrin of formula (IV), which is the first step in the process of the present invention, may be carried out in the presence of a basic compound. As the basic compound, alkali metals such as metallic sodium or metallic potassium, and hydroxides and carbonates thereof, and amine compounds such as pyridine or piperidine may be used. Also, the reaction proceeds either in the absence of a solvent or in a solvent. As the solvent, lower alcohols such as methanol, ethanol and isopropanol, ketones such as acetone and methyl ethyl ketone, ethers such as diethyl ether and dioxane, and aromatic hydrocarbons such as benzene, toluene and xylene may be used. Among these solvents, methanol and ethanol are preferable. In the reaction, the epihalogenohydrin of formula (IV) may be used in an amount of one mole per mole of the 3,4-dihydrocarbostyril of formula (II) to a large excess, but is preferably used in an amount of 5 to 10 moles per mole of the 3,4-dihydrocarbostyril of formula (II). Also, the reaction may be carried out at a temperature of 0°–150° C, but is preferably carried out at a temperature of 50°–100° C.

By the above-mentioned reaction of the first step, 5-(2',3'-epoxy)propoxy-3,4-dihydrocarbostyril derivatives (III') or 5-(3'-halogeno-2'-hydroxy)-propoxy-3,4,-dihydrocarbostyril derivates (III'') represented by the formula,

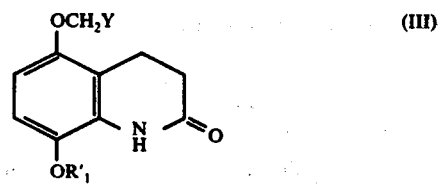

(III)

wherein R'₁ is C₁–C₄ alkyl or aralkyl and Y is

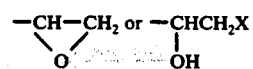

wherein X is as defined above, are obtained as an intermediate product. Usually, a mixture of the above-mentioned compounds (III') and (III'') is produced. The compound (III') is produced predominantly when the reaction is conducted in the presence of strongly basic compounds such as alkali metals and alkali hydroxides and the compound (III'') is produced predominantly when the reaction is conducted in the presence of weakly basic compounds such as organic bases, in particular piperidine and the epihalohydrin is used in excess.

These products can be separated from each other by conventional procedures, for example, fractional crystallization, but preferably are separated by column chromatography using a column packed with active alumina, silica gel or the like. Both of these compounds can be converted to the compounds of the present invention by the reaction with an alkylamine of formula (V) as described below. Regardless of the ratio of the compound (III') to the compound (III'') in the mixture, the reaction of the mixture with the alkylamine gives the compounds of the present invention and undesirable reactions or effects such as, for example, formation of by-products or reduction in yield do not occur. Therefore, it is unnecessary to isolate the above-mentioned two compounds (III') and (III'') before the reaction with the alkylamine of formula (V).

Thus, the reaction of the above-mentioned intermediate products with the alkylamine of formula (V) as the second step may be carried out with or without isolating said intermediate products from the reaction system of the first step. The reaction of the second step may be carried out either in the absence of a solvent or in a suitable solvent since the alkylamine of formula (V) used as a reactant can also act as a solvent. As the solvent, lower alcohols such as methanol, ethanol and isopropanol, ethers such as dioxane and tetrahydrofuran, and aromatic hydrocarbons such as benzene and toluene may be used. Among these solvents, methanol and ethanol are preferable. The amount of the alkylamine of formula (V) used in the reaction may be a large excess with regard to the above-mentioned intermediate products, but the alkylamine is preferably used in an amount of 6 to 8 moles per mole of the intermediate products. The reaction proceeds without heating, but it is preferable to effect the reaction at a temperature in the neighborhood of the reflux temperature (preferably of 50°–80° C).

By the above-mentioned reaction, the 3,4-dihydrocarbostyril derivatives of formula (I) according to the present invention can be obtained. Further, the compounds may be converted to a non-toxic water-soluble acid addition salt thereof by dissolving the compounds in acetone and then adding an inorganic acid such as hydrochloric acid, sulfuric acid, phosphoric acid or hydrobromic acid or an organic acid such as oxalic acid, maleic acid, fumaric acid, malic acid, tartaric acid, citric acid or ascorbic acid.

When 5-(3'-alkylamino-2'-hydroxy)propoxy-8-hydroxy-3,4-dihydrocarbostyril derivatives are desired, the 5-(3'-alkylamino-2'-hydroxy)propoxy-8-aralkoxy-3,4-dihydrocarbostyril derivatives thus obtained are then reduced. In the case of 5-(3'-alkylamino-2'-hydroxy)propoxy-8-alkoxy-3,4-dihydrocarbostyril, dealkylation is carried out by stirring the compound in the presence of excess of HX (wherein X is halogen) at room temperature.

The reduction is advantageously carried out by hydrogenating the compounds in the presence of a known hydrogenation catalyst. As the hydrogenation catalyst, palladium black, palladium-carbon, Raney nickel, platinum dioxide, etc., may be used.

The reaction proceeds advantageously in a solvent. As the solvent, water, lower alcohols such as methanol, ethanol and isopropanol, and acetic acid may be used. Also, the reaction is carried out at a temperature of 0°–100° C under atmospheric pressure, and preferably at a temperature of 20°–50° C under atmospheric pressure. Thus, the desired 5-(3'-alkylamino-2'-hydroxy)-propoxy-8-hydroxy-3,4-dihydrocarbostyrils can be easily produced.

The compounds may be converted to a non-toxic water-soluble acid addition salt thereof by dissolving the compounds in a solvent such as isopropanol and then adding an inorganic acid such as hydrochloric acid, sulfuric acid, phosphoric acid or hydrobromic acid or an organic acid such as oxalic acid, maleic acid, fumaric acid, malic acid, tartaric acid, citric acid or ascorbic acid. The 5-(3'-alkylamino-2'-hydroxy)-propoxy-8-hydroxy-3,4-dihydrocarbostyril derivatives thus obtained may be alkylated or aralkylated, if necessary, to form the corresponding 5-(3'-alkylamino-2'-hydroxy)propoxy-8-alkoxy or -aralkoxy-3,4-dihydrocarbostyril derivatives. Also, the above-mentioned dealkylation or dearalkylation may be carried out for 5-(2',3'-epoxy)propoxy-3,4-dihydrocarbostyril derivatives (III') or 5-(3'-halogeno-2'-hydroxy)propoxy-3,4-dihydrocarbostyril derivatives (III'').

As described above, the 3,4-dihydrocarbostyril derivatives of formula (I) and acid addition salts thereof obtained according to the present invention are novel compounds having β-adrenergic nerves blocking activity and hypotensive activity and useful as a remedy for angina pectoris, irregular pulse and hypertension, etc.

For example, the antagonistic activity against isoproterenol (as an indication of β-adrenergic nerves blocking activity) of the 3,4-dihydrocarbostyril derivatives of the present invention was measured according to a method as described in R. D. Robson and H. R. Kaplan, "J. Pharmacol. Exp. Therap.," Vol. 175, page 157 (1970) as follows:

Mongrel dogs of both sexes weighing 9.7 – 19.0 kg were anesthetized with pentobarbital-Na (30 mg/kg, i.v.) and fixed on their back. Anesthesia was maintained by continuous intravenous infusion of pentobarbital-Na at a rate of 4 mg/kg/hour.

Arterial blood pressure was measured from the left femoral artery with a pressure transducer (Nihon Kohden, RP-3). The left femoral vein was cannulated for i.v. injection of drugs. Heart rate was measured with a tachometer (San-ei, type 2130) treggered by the R wave of ECG (Lead II). Blood pressure and heart rate were simultaneously recorded on an ink-writing recorder (San-ei, type 145).

Test drugs were cumulatively injected at intervals of 10 minutes after reproducibility test on the positive chronotropic and hypotensive actions of a submaximal dose of 0.3 μg/kg of isoproterenol. At the time when responses of blood pressure and heart rate to these test drugs were stabilized, at about 3 minutes after injection, isoproterenol 0.3 μg/kg was injected again. Their antagonistic activities were determined from difference between responses to isoproterenol before and after administration of the test drugs and expressed as % inhibition.

The results obtained are as shown in the following table:

Table I

Antagonistic Activity against Isoproterenol
(% Inhibition of changes in BP[a] and HR[b])

| Compound | | Dose μg/kg (i.v.) | | | |
|---|---|---|---|---|---|
| | | 0.1 | 1.0 | 10 | 100 |
| 5-(OCH₂CHOHCH₂NHC(CH₃)₃)·HCl, 8-OH-3,4-dihydrocarbostyril | BP | 18.4 | 64.6 | 94.8 | 100 |
| | HR | 5.1 | 44.5 | 97.5 | 100 |
| 5-(OCH₂CHOHCH₂NHC(CH₃)₃)·HCl, 8-OCH₃-3,4-dihydrocarbostyril | BP | 40.6 | 54.4 | 77.1 | 82.2 |
| | HR | 7.0 | 8.6 | 39.8 | 80.5 |
| 5-(OCH₂CHOHCH₂NHC(CH₃)₃)·HCl, 8-OCH₂C₆H₅-3,4-dihydrocarbostyril | BP | 20.0 | 10.9 | 12.6 | 8.4 |
| | HR | 13.5 | 13.5 | 21.4 | 65.4 |

[a] Blood pressure
[b] Heart rate

The hypotensive action of the 3,4-dihydrocarbostyril derivatives of the present invention was measured as follows:

Mongrel dogs of both sexes weighing 9.7 - 19.0 kg were anesthetized with pentobarbital-Na (30 mg/kg, i.v.) and fixed on their back. Anesthesia was maintained by continuous intravenous infusion of pentobarbital-Na at a rate of 4 mg/kg/hour. After the vinyl catheter was inserted in the left femoral vein, heparin sodium, 1000 U/kg, was intravenously injected in order to prevent blood coagulation. Arterial blood pressure was measured from the left femoral artery with a pressure transducer (Nihon Kohden, RP-3). Test drugs were dissolved in 0.9% physiological saline solution and then intravenously administered with the cumulative method at intervals of 5 - 10 minutes. The results obtained are shown in the following table:

Table II

Hypotensive Action (Blood Pressure mmHg)

| Compound | Dose μg/kg (i.v.) | | | |
|---|---|---|---|---|
| | 0.1 | 1.0 | 10 | 100 |
| 5-(OCH₂CHOHCH₂NHC(CH₃)₃)·HCl, 8-OH-3,4-dihydrocarbostyril | −1.6 | −5.4 | −11.8 | −30.6 |
| 5-(OCH₂CHOHCH₂NHC(CH₃)₃)·HCl, 8-OCH₃-3,4-dihydrocarbostyril | 0.0 | −2.0 | −3.5 | −5.5 |
| 5-(OCH₂CHOHCH₂NHC(CH₃)₃)·HCl, 8-OCH₂C₆H₅-3,4-dihydrocarbostyril | −1.0 | −4.5 | −10.5 | −16.0 |

As is clear from the above table, the 3,4-dihydrocarbostyril derivatives of the present invention (0.1 - 100 μg/kg) produced dose-dependent decrease in arterial blood pressure.

The acute toxicity of the 3,4-dihydrocarbosytril derivatives of the present invention was found to be as follows:

Table III

Acute toxicity

| Compound | LD₅₀ (mg/kg) | |
|---|---|---|
| | i.v. | p.o. |
| 5-(OCH₂CHOHCH₂NHC(CH₃)₃)·HCl, 8-OH-3,4-dihydrocarbostyril | 94 | 1380 |
| 5-(OCH₂CHOHCH₂NHC(CH₃)₃)·HCl, 8-OCH₃-3,4-dihydrocarbostyril | 83 | 1210 |
| 5-(OCH₂CHOHCH₂NHC(CH₃)₃)·HCl, 8-OCH₂C₆H₅-3,4-dihydrocarbostyril | 80 | 1150 |

The following Referential Example illustrates the preparation of the 3,4-dihydrocarbostyril derivatives of formula (II) which are the starting material used in the present invention.

REFERENTIAL EXAMPLE

Step 1

16.3 Grams of 8-hydroxy-3,4-dihydrocarbostyril was suspended in 75 ml of acetic anhydride and cooled to 0° C. To the suspension was added a solution of 7.8 g of fuming nitric acid in 50 ml of glacial acetic acid dropwise while the temperature was kept at a temperature below 5° C. After the completion of addition, the mixture was stirred at a temperature below 5° C for 2 hours. 20 Grams of broken ice was added and the separated precipitate was collected by filtration, and recrystallized from dioxane. Thus, 8.5 g of a yellow amorphous substance having a melting point of more than 300° C was obtained. The product was identified as 5-nitro-8-hydroxy-3,4-dihydrocarbostyril by the analysis results of NMR, IR ($NO_2$: 1570 $cm^{-1}$, 1320 $cm^{-1}$) and elementary analysis.

Step 2

3 Grams of stannous chloride was dissolved in 5 ml of concentrated hydrochloric acid. To the solution was added 1 g of 5-nitro-8-hydroxy-3,4-dihydrocarbostyril on a boiling water bath with stirring. The separated precipitate was collected by filtration, washed with acetone and recrystallized from water. Thus, 0.9 g of needle crystals having a melting point of more than 300° C were obtained. The product was identified as 5-amino-8-hydroxy-3,4-dihydrocarbostyril hydrochloride by the analysis results of NMR, IR ($NH_2$ hydrochloride: 3280, 2600, 1590, 1500 $cm^{-1}$) and elementary analysis.

Step 3

1.0 Gram of 5-amino-8hydroxy-3,4-dihydrocarbostyril hydrochloride was dissolved in a mixture of 0.1 ml of hydrochloric acid and 40 ml of water. After dissolution, the solution was immediately filtered by suction. The filtrate was cooled to room temperature. To the solution was added a solution of 3 g of ferric chloride in a mixture of 1 ml of hydrochloric acid and 3 ml of water at a stroke with violent stirring. The mixture was stirred at room temperature for 1 hour. The separated crystals were collected by filtration and recrystallized from ethyl acetate. Thus, 0.6 g of yellow needle crystals having a melting point of 185°–188° C (decomposition) was obtained. The product was identified as 5,8-dioxo-3,4,5,8-tetrahydrocarbostyril by the analysis results of NMR, IR and elementary analysis.

Step 4

0.8 Gram of 5,8-dioxo-3,4,5,8-tetrahydrocarbostyril was suspended in 30 ml of water and sulfur dioxide was then introduced into the suspension at room temperature with stirring. The separated crystals were collected by filtration and recrystallized from water. Thus, 0.5 g of colorless needle crystals having a melting point of 228°–230° C were obtained. The product was identified as 5,8-dihydroxy-3,4-dihydrocarbostyril by the analysis results of NMR, IR and elementary analysis.

Step 5

1.8 Grams of 5,8-dihydroxy-3,4-dihydrocarbostyril and 1.6 g of potassium carbonate were suspended in a mixture of 150 ml of acetone and 50 ml of water. To the suspension was added 1.0 g of dimethyl sulfate. Th mixture was heated under reflux for 8 hours. After cooling, acetone was removed by distillation under reduced pressure. Water was added and the reaction product was extracted with chloroform. The chloroform layer was washed with a dilute aqueous sodium hydroxide solution and then with water. The chloroform layer was dried over anhydrous sodium sulfate and chloroform was removed by distillation. The residue was recrystallized from methanol to obtain 0.5 g of colorless prism crystals having a melting point of 171°–173.5° C. The product was identified as 5,8-dimethoxy-3,4-dihydrocarbostyril by the analysis results of NMR, IR and elementary analysis. The above-mentioned washings were combined, acidified with concentrated hydrochloric acid, and then extractd with chloroform. The chloroform layer was dried over anhydrous sodium sulfate, and chloroform was removed by distillation. The residue was recrystallized from ethanol to obtain 1.0 g of colorless needle crystals having a melting point of 202°–204° C. The product was identified as 5-hydroxy-8-methoxy-3,4-dihydrocarbostyril by the analysis results of NMR, IR and elementary analysis.

The following examples illustrate the present invention.

EXAMPLE 1

To 1.5 g of 5-hydroxy-8-methoxy-3,4-dihydrocarbostyril were added 4.5 g of epichlorohydrin and 3 drops of piperidine. The mixture was heated at 90°–95° C for 2 hours. The reaction liquid was concentrated under reduced pressure, and the residue was dissolved in chloroform. The solution was washed with a dilute aqueous sodium hydroxide solution and then with water, and was dried over anhydrous sodium sulfate. Chloroform was removed by distillation under reduced pressure to obtain 1.2 g of an intermediate product, which was separated by chromatography into the two components which were identified as 5-(2',3'-epoxy)-propoxy-8-methoxy-3,4-dihydrocarbostril and 5-(3'-chloro-2'-hydroxy)propoxy-8-methoxy-3,4-dihydrocarbostyril respectively by the analysis results of NMR, IR and elementary analysis. Further, 1.2 g of the above-mentioned intermediate product was dissolved in 20 ml of methanol, and 2.5 g of tert-butylamine was added. The mixture was heated under reflux for 5 hours. The reaction liquid was concentrated to dryness under reduced pressure. The residue was dissolved in dilute hydrochloric acid. The solution was washed with chloroform, neutralized with sodium bicarbonate, and then concentrated under reduced pressure. The residue was extracted with ethanol. Ethanol was removed by distillation under reduced pressure. The residue was dissolved in acetone and a solution of maleic acid in acetone was added. The separated crystals were collected by filtration and recrystallized from ethanol to obtain 0.5 g of a white powdery product having a melting point of 201°–202° C (decomposition). The product was identified as 5-(3'-tert-butylamino-2'-hydroxy)propoxy-8-methoxy-3,4-dihydrocarbostyril maleate by the analysis results of NMR, IR and elementary analysis.

EXAMPLE 2

To 4.0 g of 5-hydroxy-8-benzyloxy-3,4-dihydrocarbostyril were added 8.5g of epichlorohydrin and 10 drops of piperidine. The mixture was heated at 90°–94° C for 2 hours. The reaction liquid was concentrated under reduced pressure, and the residue was dissolved in chloroform. The solution was washed with a dilute aqueous sodium hydroxide solution and then with water, and was dried over anhydrous sodium sulfate. Chloroform was removed by distillation under reduced presure to obtain 4.0 g of an oily intermediate product, which was identified as a mixture of 5-(2',3'-epoxy)-propoxy-8-benzyloxy-3,4-dihydrocarbostyril and 5-(3'-chloro-2'-hydroxy)propoxy-8-benzyloxy-3,4-dihydrocarbostyril by the analysis results of NMR, IR and elementary analysis. Further, 4.0 g of the above-mentioned intermediate product was dissolved in 40 ml of methanol, and 6.5 g of tert-butylamine was added. The mixture was heated under reflux for 3 hours. The reaction liquid was concentrated under reduced pressure. The residue was recrystallized from isopropanol to obtain 2.0 g of colorless flaky crystals having a melting point of 124°–126° C. The product was identified as 5-(3'-tert-butylamino-2'-hydroxy)propoxy-8-benzyloxy-3,4-dihydrocarbostyril by the analysis results of NMR, IR and elementary analysis.

EXAMPLE 3

4.0 Grams of the intermediate product obtained in the same manner as in Example 2 was dissolved in 50 ml of methanol, and 6 g of isopropylamine was added. The mixture was heated under reflux for 3 hours. Similar treatments as in Example 2 gave 2.0 g of colorless plate crystals having a melting point of 132° – 135° C. The product was identified as 5-(3'-isopropylamino-2'-hydroxy)propoxy-8-benzyloxy-3,4-dihydrocarbostyril by the analysis results of NMR, IR and elementary analysis.

EXAMPLE 4

1.4 Grams of 5-hydroxy-8-benzyloxy-3,4-dihydrocarbostyril was dissolved in 30 ml of methanol, and 0.4 g of sodium ethylate was added. The mixture was heated under reflux for 30 minutes, and 1.6 g of epichlorohydrin was then added. The mixture was heated under reflux for 2 hours. The reaction liquid was concentrated to dryness under reduced pressure, and the residue was dissolved in chloroform. The solution was washed with a dilute aqueous sodium hydroxide solution and then with water, and was dried over anhydrous sodium sulfate. Chloroform was removed by distillation under reduced pressure to obtain 1.0 g of an oily intermediate product. The product was identified as a mixture of 5-(2',3'-epoxy)propoxy-8-benzyloxy-3,4-dihydrocarbostyril and 5-(3'-chloro-2'-hydroxy)propoxy-8-benzyloxy-3,4-dihydrocarbostyril by the analysis results of NMR, IR and elementary analysis. Further, 1.0 g of the above-mentioned intermediate product was dissolved in 20 ml of methanol, and 2 g of sec-butylamine was added. The mixture was heated under reflux for 3 hours. The reaction liquid was concentrated to dryness under reduced pressure. The residue was recrystallized from isopropanol to obtain 0.6 g of colorless flaky crystals having a melting point of 111° – 112° C. The product was identified as 5-(3'-sec-butylamino-2'-hydroxy)propoxy-8-benzyloxy-3,4-dihydrocarbostyril by the analysis results of NMR, IR and elementary analysis.

EXAMPLE 5

1.5 Grams of 5-(3'-tert-butylamino-2'-hydroxy)-propoxy-8-benzyloxy-3,4-dihydrocarbostyril was dissolved in 30 ml of methanol, and hydrogen was absorbed by the solution in the presence of 0.2 g of 10% palladium-carbon at room temperature while the solution was stirred. The catalyst was removed by filtration, and the filtrate was concentrated under reduced pressure. Th residue was dissolved in isopropanol and a solution of maleic acid in acetone was added. The separated crystals were collected by filtration and recrystallized from ethanol to obtain 1.0 g of colorless needle crystals having a melting point of 187° – 190° C (decomposition). The product was identified as 5-(3'-tert-butylamino-2'-hydroxy)-propoxy-8-hydroxy-3,4-dihydrocarbostyril maleate by the analysis results of NMR, IR and elementry analysis.

EXAMPLE 6

1.0 Gram of 5-(3'-isopropylamino-2'-hydroxy)-propoxy-8benzyloxy-3,4-dihydrocarbostyril was dissolved in 30 ml of methanol, and hydrogen was absorbed by the solution in the presence of 0.15 g of 10% palladium-carbon at room temperature while the solution was stirred. Similar treatments as in Example 5 gave 0.5 g of colorless needle crystals having a melting point of 162° – 165° C (decomposition). The product was identified as 5-(3'-isopropylamino-2'-hydroxy)-propoxy-8-hydroxy-3,4-dihydrocarbostyril maleate by the analysis results of NMR, IR and elementary analysis.

EXAMPLE 7

0.2 Gram of 5-(3'-sec-butylamino-2'-hydroxy)-propoxy-8-benzyloxy-3,4-dihydrocarbostyril was dissolved in 20 ml of methanol, and hydrogen was absorbed by the solution in the presence of 0.05 g of 10% palladium-carbon at room temperature while the solution was stirred. Similar treatments as in Example 5 gave 0.1 g of colorless needle crystals having a melting point of 175°–178° C (decomposition). The product was identified as 5-(3'-sec-butylamino-2'-hydroxy)-propoxy-8-hydroxy-3,4-dihydrocarbostyril maleate by the analysis results of NMR, IR and elementary analysis.

What is claimed is:

1. A compound of the formula,

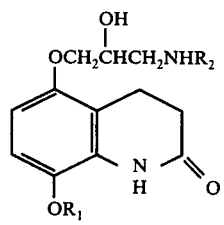

wherein $R_1$ is hydrogen, $C_1$–$C_4$ alkyl, benzyl or phenethyl and $R_2$ is $C_1$–$C_4$ alkyl or a pharmaceutically acceptable acid addition salt thereof.
2. 5-(3'-tert-Butylamino-2'-hydroxy)propoxy-8-hydroxy-3,4-dihydrocarbostyril or a pharmaceutically acceptable acid addition salt thereof.
3. 5-(3'-Isopropylamino-2'-hydroxy)propoxy-8-hydroxy-3,4-dihydrocarbostyril or a pharmaceutically acceptable acid addition salt thereof.
4. 5-(3'-sec-Butylamino-2'-hydroxy)propoxy-8-hydroxy-3,4-dihydrocarbostyril or a pharmaceutically acceptable salt thereof.
5. 5-(3'-tert-Butylamino-2'-hydroxy)propoxy-8-methoxy-3,4-dihydrocarbostyril or a pharmaceutically acceptable acid addition salt thereof.
6. 5-(3'-tert-Butylamino-2'-hydroxy)propoxy-8-benzyloxy-3,4-dihydrocarbostyril or a pharmaceutically acceptable acid addition salt thereof.
7. 5-(3'-Isopropylamino-2'-hydroxy)propoxy-8-benzyloxy-3,4-dihydrocarbostyril or a pharmaceutically acceptable acid addition salt thereof.
8. 5-(3'-sec-Butylamino-2'-hydroxy)propoxy-8-benzyloxy-3,4-dihydrocarbostyril or a pharmaceutically acceptable acid addition salt thereof.

* * * * *